United States Patent
Farin

(10) Patent No.: US 7,226,465 B1
(45) Date of Patent: Jun. 5, 2007

(54) SURGICAL INSTRUMENT

(75) Inventor: Gunter Farin, Tubingen (DE)

(73) Assignee: ERBE Elektromedizin GmbH, Tubingen (DE)

( * ) Notice: Subject to any disclaimer, the term of this patent is extended or adjusted under 35 U.S.C. 154(b) by 0 days.

(21) Appl. No.: 09/958,006

(22) PCT Filed: Mar. 31, 2000

(86) PCT No.: PCT/EP00/02907

§ 371 (c)(1),
(2), (4) Date: Nov. 27, 2001

(87) PCT Pub. No.: WO00/59391

PCT Pub. Date: Oct. 12, 2000

(30) Foreign Application Priority Data

Apr. 1, 1999 (DE) ................. 199 15 062

(51) Int. Cl.
A61B 17/28 (2006.01)
A61B 18/18 (2006.01)

(52) U.S. Cl. ...................... 606/205; 606/207

(58) Field of Classification Search ........ 606/205–213, 606/170, 171, 180, 50–52, 41–49
See application file for complete search history.

(56) References Cited

U.S. PATENT DOCUMENTS 2,068,721 A 1/1937 Wappler et al.
4,011,872 A * 3/1977 Komiya .................. 606/47
5,408,409 A 4/1995 Glassman et al.
5,718,703 A 2/1998 Chin
5,754,741 A 5/1998 Wang et al.
5,882,206 A 3/1999 Gillio
6,923,806 B2 * 8/2005 Hooven et al. ............. 606/41

FOREIGN PATENT DOCUMENTS

| EP | 0 400 288 A2 | 12/1990 |
| EP | 0 795 301 A1 | 9/1997 |
| WO | WO 96/09587 | 3/1996 |
| WO | WO 97/17033 | 5/1997 |
| WO | WO 98/52479 | 11/1998 |

* cited by examiner

Primary Examiner—Vy Q. Bui
(74) Attorney, Agent, or Firm—Merchant & Gould P.C.

(57) ABSTRACT

A surgical instrument is provided that comprises at least three, and preferably four forceps elements with hook-shaped distal sections having free ends and associated proximal sections that are connected to actuators for moving the distal sections. The distal sections are shaped and movably disposed in such a way that they can be brought together to form a single hook, which can be used in particular for blunt dissection, and can be combined in groups, for example groups of two, to form at least one pair of forceps which can be moved with respect to one another in order to grasp tissue or spread it apart. This design allows a single instrument to be used for many different dissection procedures.

29 Claims, 2 Drawing Sheets

SURGICAL INSTRUMENT

This application is a 371 of PCT/EP00/02907 filed Mar. 31, 2000

FIELD OF THE INVENTION

The present invention relates to a surgical instrument with a plurality of functions.

DESCRIPTION OF THE PRIOR ART

U.S. Pat. No. 4,043,342 discloses a cutting instrument for high-frequency surgery in which a thin metal needle, which serves as cutting electrode, is enclosed within a metal sheath serving as neutral electrode, against which the cutting electrode is insulated, and is arranged so that the cutting electrode projects from or can be pushed out of the sheath in the axial or radial direction. Such an instrument is suitable, for instance, for making fine cuts. The thinner the metal needle is, the less high-frequency current is needed for cutting and the slighter is the thermal damage to the cut edges. However, a thin metal needle is at greater risk of bending or breaking off, so that the tissue can easily be accidentally damaged. Blunt dissection is not possible with this arrangement, so that when it is needed, another instrument must be used for that purpose. Exchanging instruments costs time and effort, which increases the risk to the patient.

U.S. Pat. No. 4,931,047 discloses a surgical instrument in which, in order to avoid an intraoperative exchange of instruments, a high-frequency current can be applied simultaneously or in alternation with ultrasonic aspiration by way of the same applicator tip. With this instrument, again, blunt dissection is impossible.

For blunt dissection a variety of instruments are known, but these must be exchanged for other instruments during the operation if, for example, tissue must be raised on a hook, spread apart or gripped in alternation.

The object of the present invention is to provide a surgical instrument which enables a plurality of dissection possibilities to be implemented in a simple manner with no exchange of instruments.

SUMMARY OF THE INVENTION

According to the present invention there is provided a surgical instrument comprising at least three forceps elements having with hook-shaped distal sections, each with a free end, and associated proximal sections; actuators connected to the proximal sections for moving the distal sections; the distal sections being shaped and movably disposed such that they can be brought together to form a single hook which can be used for blunt dissection and can be combined in groups to form at least one pair of forceps which can be used to grasp tissue or spread it apart. The instrument is thus capable of carrying out a large number of different dissection steps.

Preferably, four forceps elements are provided which can be combined in groups of two elements to define at least one pair of forceps which can be used to grasp tissue or spread it apart.

Preferably also, electrode devices are provided at the distal sections, or the distal sections themselves are constructed as electrode devices, which are connected to controllable HF generators so as to apply a high-frequency current, in particular for coagulating tissue that has been grasped by the forceps elements or brought into contact therewith. In this case the proximal sections are preferably insulated substantially all around their periphery, so that unintended injuries can be avoided.

In a preferred embodiment of the invention, a cutting means is provided that can be moved with respect to the forceps elements in order to cut tissue. Thus the instrument can be used both for blunt dissection and for cutting tissue that, for example, has been placed on the hook. Preferably the cutting means provided here comprises an electrode, or is constructed as an electrode, and is connected to a controllable HF generator so that it can transect or cut tissue by means of a high-frequency electric current.

Such a cutting means can be moved from an external position toward the distal sections, but it is particularly advantageous for the cutting means to be designed so as to be accommodated between the distal and/or the proximal sections when these are assembled to form a hook. As a result, an unintentional injury to the tissue is prevented. At the same time, when the cutting means is constructed as a thin wire, there is also no longer a risk of injury to the operator when the instrument is in its "resting state", i.e. when the distal sections have been brought together.

Preferably, the actuators associated with the proximal sections include a tubular shaft within which the proximal sections are guided and held. The movements of the proximal and hence also the distal sections can be induced in a manner known per se. At the proximal end of the tubular shaft appropriate manipulators are provided for moving the distal sections.

The instrument is preferably of modular construction, such that the parts relevant to hygiene can be rapidly, easily and safely disinfected and sterilized. This is preferably achieved by making the effectors, which include the proximal sections and the tubular shaft, separable from the actuators. As a result, cleaning and sterilization become unproblematic.

The tubular shaft can in addition be used to supply a rinsing solution or a protective gas, for example for coagulating or cutting, or can be connected to suction devices in such a way that body fluids or previously introduced rinsing liquid can be sucked away.

The liquid or gas that is supplied can also serve to cool the instruments when a high-frequency current is being applied.

The distal sections can be shaped in various ways, depending on the intended application of the instrument in accordance with the invention. If it is to be used mainly for dissection, the shape of the distal sections can be made optimal for this purpose. For example, the instrument can be made to resemble a round, one-piece dissection hook, but with subdivisions in the longitudinal direction that separate it into several identical or differing parts, called "pins" in the following. If it is primarily intended for the separation or cutting of tissue structures, which requires a prophylactic hemostasis to be produced by thermal coagulation, the pins can have the optimal shape for this purpose. In this case, for instance, two pins or a pair of pins can have a rounded, cylindrical shape and two other pins, or a second pair of pins, can be shaped like a cylindrical shell, so that tissue to be thermally coagulated for prophylactic hemostasis is grasped in each of two places between a pin in the form of a solid cylinder and an associated cylindrical shell.

To enable the effectors, i.e. the distal sections and where necessary the cutting electrode(s), to be coordinated as required for the particular application and reliably put into the appropriate working or resting position, the above-mentioned actuators are disposed at the proximal end of the tubular shaft. Manual actuators suitable for this purpose are levers or press-keys, finger-holes, and sliders, whereas automatic actuators can take the form of pneumatic, hydraulic, electromagnetic and/or electromotor energy/force transducers. The actuators can be triggered either individually or automatically in a preprogrammed sequence, for example by way of key depression, switching or even verbal commands.

Various embodiments of the present invention will now be described by way of example with reference to the accompanying drawings.

DESCRIPTION OF THE PREFERRED EMBODIMENTS

Figure 1:
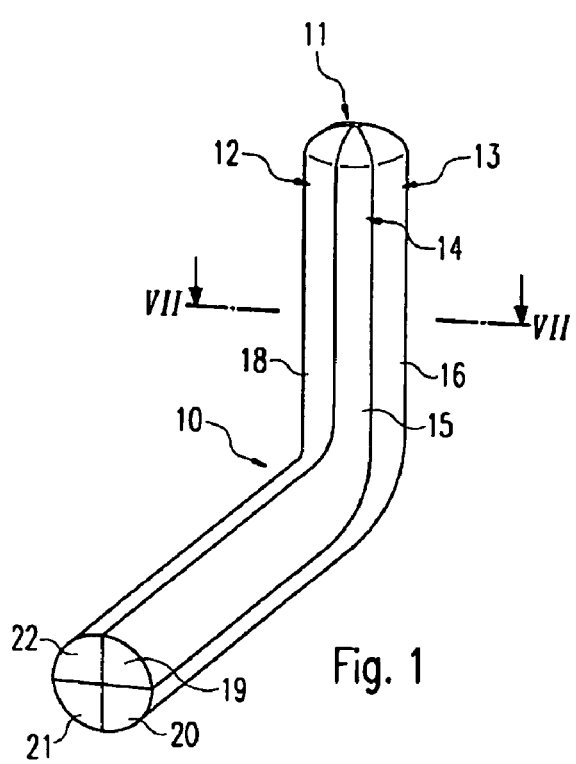
FIG. 1 is a perspective diagram of a distal section of a surgical instrument according to the invention.

In the following description, the same reference numerals are used for identical parts or parts with identical actions.

In the surgical instrument shown in FIG. 1, a hook 10 is formed by four forceps elements 11, 12, 13 and 14, each of which comprises a distal section 15, 16, 17 and 18 as well as a proximal section 19, 20, 21 and 22. The proximal sections 19-22 are connected to activation devices such as are described above, in a manner not shown here.

Figure 2:
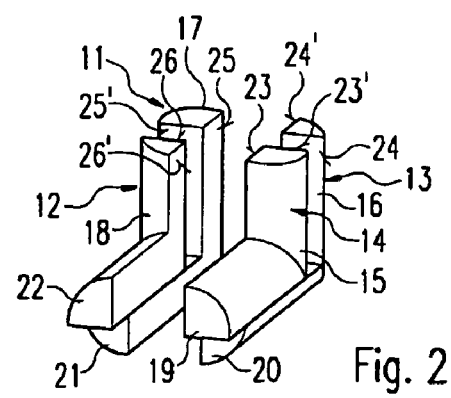
FIG. 2 is a view of a portion of the instrument of FIG. 1 showing the distal sections all separated from one another in order indicate the function of the instrument.
Figure 3:
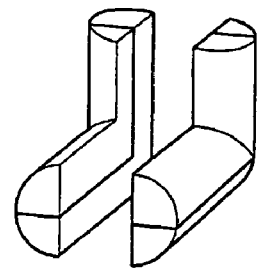
FIG. 3 is a view similar to FIG. 2, but with the distal sections put together to form two pairs.

The proximal sections 19-22 can be moved in a manner that is shown in particular in FIG. 2. That is, the two proximal sections 19 and 22 on the upper side of the hook 10 can be displaced with respect to the underlying proximal sections 20 and 21, along their long axes, so that the forceps elements 13 and 14 move away from the forceps elements 11 and 12 to form a gap that has a forceps function, i.e. a spreading and clamping function. Furthermore, the proximal sections 19 and 20 can be moved away from the proximal sections 20 and 21, so that a space is left free between the distal sections 15 and 18 as well as between 16 and 17; hence these distal sections or forceps elements can be used to grasp tissue or also to spread tissue apart, as shown in particular in FIG. 3. That is, with the instrument shown here blunt dissection can be performed with a number of different possible movements; in particular, tissue can be lifted up on the hook 10, can be spread apart in two directions perpendicular to one another (also simultaneously, where necessary), or gripped as though by forceps in the same two directions.

Figure 4:
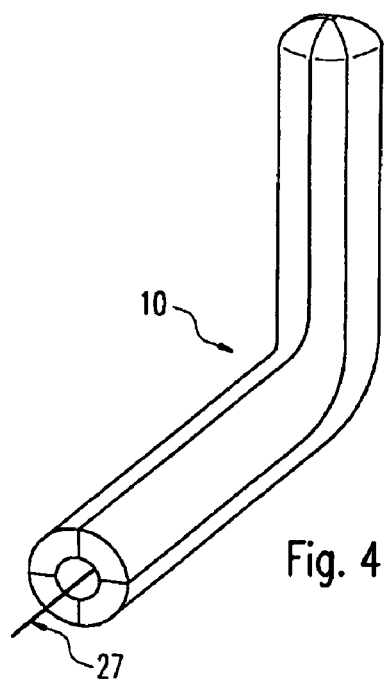
FIG. 4 is a view similar to that of FIG. 1 but of a second embodiment of the invention.
Figure 6:
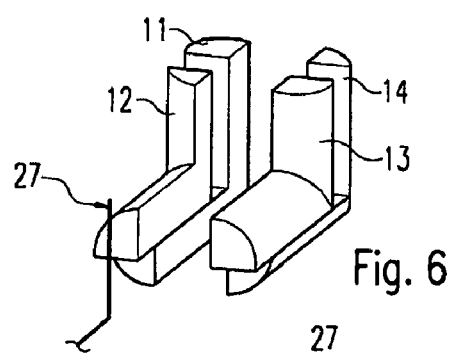
FIG. 6 is a perspective view of a portion of a third embodiment of the invention similar to that shown in FIGS. 1-3 but with the addition of a cutting electrode.
Figure 5:
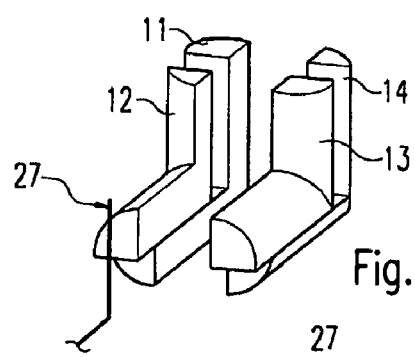
FIG. 5 is a view of a portion of the instrument of FIG. 4 in a position corresponding to that of the first embodiment shown in FIG. 3.
Figure 7:
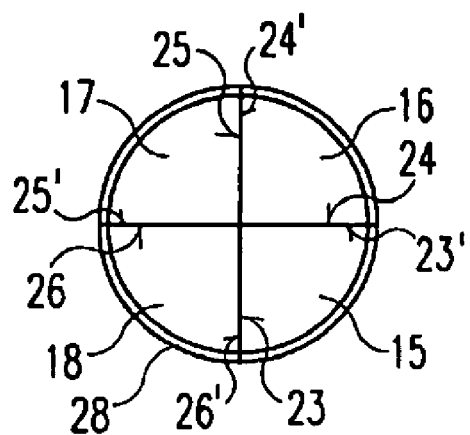
FIG. 7 is a sectional view along the line VII-VII of FIG. 1.

Preferably the distal sections 15-18, as shown particularly in FIG. 7, are enclosed over their entire periphery by an insulating layer 28 and are otherwise made of metal, so that the surfaces in the interior, when the sections are assembled to form the hook 10, form electrode sections 23, 23' to 26, 26'. These electrode sections 23, 23' to 26, 26' can be connected to high-frequency generators in such a way that between each two adjacent electrodes 23', 24; 24', 25; 25', 26 and 26', 23 a coagulation current can be passed through the tissue that is clamped between these two electrode sections, i.e. between the associated distal sections or forceps elements. For example, when a vessel is clamped between two forceps elements 11-14 and a coagulation current is applied, the vessel can be coagulated at two sites simultaneously for prophylactic hemostasis. After such coagulation a cutting electrode 27, such as is shown in FIGS. 4 to 6, can be guided between the separated forceps elements 11, 12; 13, 14 in the direction toward the clamped tissue, and an appropriate HF cutting current, either monopolar, by the use of a neutral electrode, or bipolar, between cutting electrode and at least one of the forceps elements, can then be applied to transect the clamped tissue. Because coagulation has already taken place, the cutting process cannot cause bleeding. In the arrangement shown in FIGS. 4 and 5, the cutting electrode 27 is disposed in a cavity enclosed by the distal sections 15-18 and by the proximal sections 19-22; hence it is exposed only when the forceps elements 11-14 are moved apart from one another. Therefore when the forceps elements are in the closed state, forming the hook 10, the electrode 27 is protected.

Figure 8:
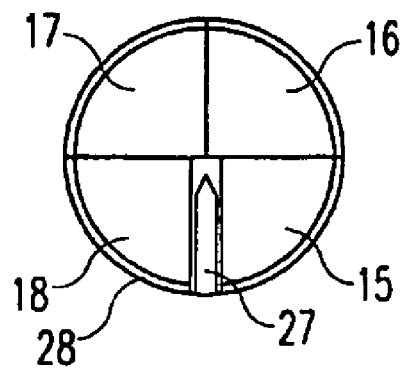
FIGS. 8 and 9 are transverse sectional views similar to FIG. 7 but showing other embodiments of the invention.
Figure 9:
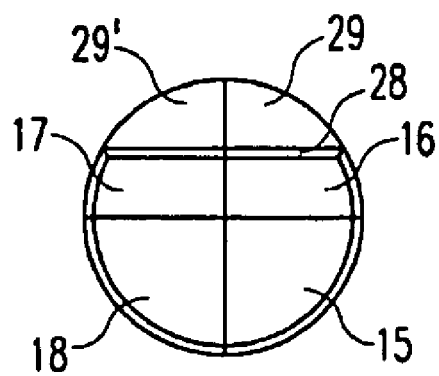

In the embodiment shown in FIG. 8, the cutting electrode 27 has the shape of a knife and occupies a space between two of the distal sections, 15 and 18. Functionally, this arrangement corresponds to that shown in FIG. 5; that is, the cutting device 27 is protected when the apparatus is assembled to form the hook 10.

The forceps elements 11-14 can comprise, in addition to the internally positioned electrode sections 23, 23' to 26, 26', external electrode sections 29, 29' that can be brought into contact with tissue in order to bring about large-scale coagulation, if this should be necessary. The function of the forceps elements 11-14, and of their electrode sections 23, 23' to 26, 26', is not thereby impaired if an insulating layer 28 is provided between the external electrode 29 and the associated electrode section. Obviously, other combinations are also conceivable in this regard, so that coagulation of this kind can be accomplished by contact not only with a front surface of the hook 10 but also with side surfaces or even with merely its tip.

The coagulation current can also be applied in other combinations of the electrode device. For example, tissue can be gripped in two places, between the forceps elements 11 and 12 and between the elements 13 and 14, and a coagulation current can be made to flow between these two pairs of forceps elements, so that all the tissue contained between the pairs is coagulated. In this aspect in particular, i.e. with respect to the available variations of current flow path, the present invention represents a considerable improvement over the available prior art.

What is claimed is:

1. A surgical element comprising,
    at least three forceps elements, each forceps element having a distal section at a free end thereof and an associated longitudinal proximal section; and
    actuators adapted and configured for effecting motion of each of said forceps elements, relative to each other wherein
    said distal section of each of said forceps element extends longitudinally from the respective proximal section at an identical orientation and an identical non-zero angle.

2. The surgical instrument of claim 1, wherein the form of said distal sections is such that, when said distal sections are in abutment a resultant radial outer surface has a smoothly and continuously curved shape and a resultant tip surface has a blunt, dome-like shape.

3. The surgical instrument of claim 1, wherein the form of said distal sections is such that, when said distal sections are in abutment, a resultant outer surface has a cylindrical shape.

4. The surgical instrument of claim 1, wherein the form of said distal sections is such that, when one or more of said distal sections is not in abutment with others of said distal sections, inner surfaces of the distal sections are exposed that are suitable for grasping tissue by moving the distal sections toward abutment.

5. The surgical instrument of claim 1, wherein each of said distal sections comprises:
at least one first abutment surface adapted and configured to matingly abut a respective abutment surface of a first other of said distal sections when said distal sections are in abutment, and
at least one second abutment surface configured and adapted to matingly abut, when said distal sections are in abutment, a respective abutment surface of a second other of said distal sections that is different from said first other distal section.

6. The surgical instrument of claim 1, wherein said longitudinal proximal sections are oriented in parallel.

7. The surgical instrument of claim 1, wherein said forceps elements are separate from one another.

8. The surgical instrument of claim 1, wherein said at least three forceps elements is four forceps elements.

9. The surgical instrument of claim 1, comprising:
at least one electrode devices provided at any of said distal sections; and
at least one controllable high frequency generators for connection with one or more of said electrode devices, wherein
said electrode devices and said controllable high frequency generators are configured and adapted to supply a coagulation current to tissue that is grasped or brought into contact with one or more of said forceps elements.

10. The surgical instrument of claim 9, wherein one or more of said distal sections are configured and adapted as said one or more electrode devices.

11. The surgical instrument of claim 10, wherein at least one of said proximal sections and the associated distal section are insulated around substantially their entire periphery.

12. The surgical instrument of claim 1, comprising a tissue cutting means configured and adapted to be moveable with respect to said forceps elements.

13. The surgical instrument of claim 12, comprising:
a controllable high frequency generator, wherein
said tissue cutting means comprises an electrode,
said tissue cutting means is connected to said controllable high frequency generator; and
said tissue cutting means and said controllable high frequency generator are configured and adapted for transecting or cutting tissue by means of a high frequency electrical current.

14. The surgical instrument of claim 12, wherein said distal sections, said proximal sections and said tissue cutting means are configured and adapted such that said tissue cutting means can be enclosed by at least one of said distal sections and said proximal sections when said distal sections are in abutment.

15. The surgical instrument of claim 1, wherein one or more of said actuators comprise a tubular shaft configured and adapted for holding a guiding one or more of said proximal sections.

16. The surgical instrument of claim 15, comprising one or more manipulators provided at a proximal end of one or more of said tubular shafts for effecting motion of respective distal sections.

17. A method of operating a surgical instrument, the surgical instrument including at least three forceps elements, each forceps element having a distal section at a free end thereof and an associated longitudinal proximal section, the distal section of each of the forceps elements extending longitudinally from the respective proximal section at an identical orientation and an identical non-zero angle, the method comprising:
moving each of at least two of the forceps elements relative to each other into a first configuration; and
moving the at least two forceps elements relative to each other into a second configuration different from the first configuration.

18. The method of claim 17, wherein the first configuration includes the distal section of the at least three forceps elements in abutment with each other.

19. The method of claim 18, wherein the first configuration defines a radial outer surface having a smoothly and continuously curved shape and a tip surface having a hemispherical shape.

20. The method of claim 17, wherein the resultant outer surface of the at least three forceps elements in abutment with each other has a cylindrical shape.

21. The method of claim 17, wherein the second configuration includes the distal section of at least two forceps elements in abutment with each other an at least one forceps element spaced apart from the at least two forceps elements that are in abutment with each other.

22. The method of claim 17, further comprising moving the at least three forceps elements relative to each other into a third configuration different from the first and second configurations.

23. The method of claim 17, wherein the distal sections are shaped such that when one or more of the distal sections is not in abutment with others of the distal sections, exposed surfaces of the distal section are arranged for grasping tissue by moving the distal sections toward abutment.

24. The method of claim 17, wherein each distal section includes at least first and second abutment surfaces configured and arranged to engage distal sections of at least two different forceps elements.

25. The method of claim 17, further comprising arranging the longitudinal proximal sections in parallel with each other.

26. The method of claim 25, wherein the longitudinal proximal sections remain in parallel with each other when moving the at least two forceps elements relative to each other into the first and second configurations.

27. The method of claim 17, wherein the at least three forceps elements includes four forceps elements.

28. The method of claim 27, wherein the first configuration includes a first pair of forceps elements in abutment with each other and a second pair of forceps elements in abutment with each other, the first and second pairs of forceps elements being spaced apart from each other and movable relative to each other.

29. The method of claim 17, wherein the non-zero angle is about 90°.

* * * * *